(12) United States Patent
Zoellner

(10) Patent No.: US 7,081,034 B1
(45) Date of Patent: Jul. 25, 2006

(54) NURSING BRA WITH POCKET

(76) Inventor: Nicole Zoellner, 600 Olympic St., Sun Prairie, WI (US) 53590

( * ) Notice: Subject to any disclaimer, the term of this patent is extended or adjusted under 35 U.S.C. 154(b) by 0 days.

(21) Appl. No.: 11/171,741

(22) Filed: Jun. 30, 2005

(51) Int. Cl.
| A41C 3/04 | (2006.01) |
| A61F 7/10 | (2006.01) |
| A41D 1/20 | (2006.01) |
| A41C 3/12 | (2006.01) |

(52) U.S. Cl. .............................. 450/54; 2/104; 607/108
(58) Field of Classification Search ............ 450/36–38, 450/54–57; 2/104, 267, 268; 623/7, 8; 607/108, 607/113, 115
See application file for complete search history.

(56) References Cited

U.S. PATENT DOCUMENTS

| 2,501,860 | A | * | 3/1950 | Becker | 450/36 |
| 2,925,816 | A | * | 2/1960 | Rosenthal | 450/37 |
| 4,024,876 | A | * | 5/1977 | Penrock | 450/48 |
| 4,335,728 | A | * | 6/1982 | Fildan | 450/36 |
| 6,063,110 | A | * | 5/2000 | Stedman | 607/108 |
| 6,083,079 | A | * | 7/2000 | Pearson | 450/1 |
| 6,346,027 | B1 | * | 2/2002 | Merkovsky | 450/37 |
| 6,394,879 | B1 | * | 5/2002 | Paige | 450/38 |
| 6,464,717 | B1 | * | 10/2002 | Smith et al. | 607/108 |

* cited by examiner

*Primary Examiner*—Gloria M. Hale
(74) *Attorney, Agent, or Firm*—Ryan Kromholz & Manion, S.C.

(57) ABSTRACT

A nursing bra comprised of two cups with an outer pocket/flap in each cup for holding a thin circular heating/cooling device in place. This pocket is a full piece of fabric with an opening at the upper center portion of the garment that holds the heating/cooling device in place. The heating/cooling device provides relief from engorgement, plugged ducts, mastitis and other general nursing pain. There is also a rear panel comprised of two cups with openings in each cup for nursing a baby. The front and rear panel coexist, forming a supportive and comfortable bra. The removable front, outer panel is connected to the rear panel at the base, which allows for the upper portion of the front panel to be lowered allowing the nipple, and surrounding area of the woman's breast to be exposed for nursing.

17 Claims, 2 Drawing Sheets

NURSING BRA WITH POCKET

BACKGROUND OF THE INVENTION

1. Field of the Invention

This invention relates to nursing bras for women, more specifically a bra that provides support, and also has a pocket to hold a heating/cooling device in place over the breast. This pocket is a full piece of fabric that acts as a shield/barrier between the heating/cooling device and the breast of nursing mothers.

2. Description of Related Art

The current state of the art provides numerous types of bras for use while nursing infants. Such bras have been patented to Alberts (U.S. Pat. No. 2,679,048) and La Rue (U.S. Pat. No. 2,121,088) and one issued to Strauss (U.S. Pat. No. 206,906) for a corset that allows for breast feeding. Patent issue to Mattson (U.S. Pat. No. 1,094,158) and Fowler (U.S. Pat. No. 5,326,305) both disclose garments with moisture shields to protect from leakage of lacteal fluids. Also, the patent issued to Weber-Unger (U.S. Pat. No. 4,164,228) is for a pad to be used with a nursing bra. A patent was given to Raimondo (U.S. Pat. No. 6,659,841), which has a pocket positioned over each bra cup and secured to the inner surface of the cup. This pocket overlays approximately one-half of the inner surface, but does not cover any part of the opening. U.S. Pat. No. 6,464,717, "Bra with hot/cold inserts," describes a vest that can be worn over a person's chest. However, this product does not direct the heating/cooling element to the necessary placement as defined by a woman's breast, and is not advantageous to be worn as a nursing bra.

While these references, specifically those having a removable absorbent pad, have helped women manage problems dealing with leakage, they do not necessarily address much of the pain and discomfort a woman may experience. It is common for women nursing infant children to experience general pain associated with nursing and engorgement, plugged ducts, and/or mastitis. Such periods can be extremely painful. To help ease this pain, medical professionals have recommended applying heat or cool compresses to the affected breast respectively. It would be beneficial to provide a nursing bra that would ease such pains.

SUMMARY OF THE INVENTION

The present invention expands the prior art by allowing a nursing mother to apply heat or cold to their breasts without having to hold the device in place. This invention would allow a quick, convenient, inconspicuous way of holding a reusable heating/cooling device on the breast while other activities are performed.

An object of the present invention is to provide a woman's supportive undergarment.

An additional object provides a comfortable area for nursing without having to remove the undergarment.

Another object is to provide an area for a heating/cooling pad to be placed and held securely in the bra by a pocket to relieve pain from nursing, engorement, plugged ducts, and mastitis.

Finally, object contains a full piece of fabric that acts as a barrier between the heating/cooling device and the breast.

DESCRIPTION OF THE PREFERRED EMBODIMENT

Figure 1:
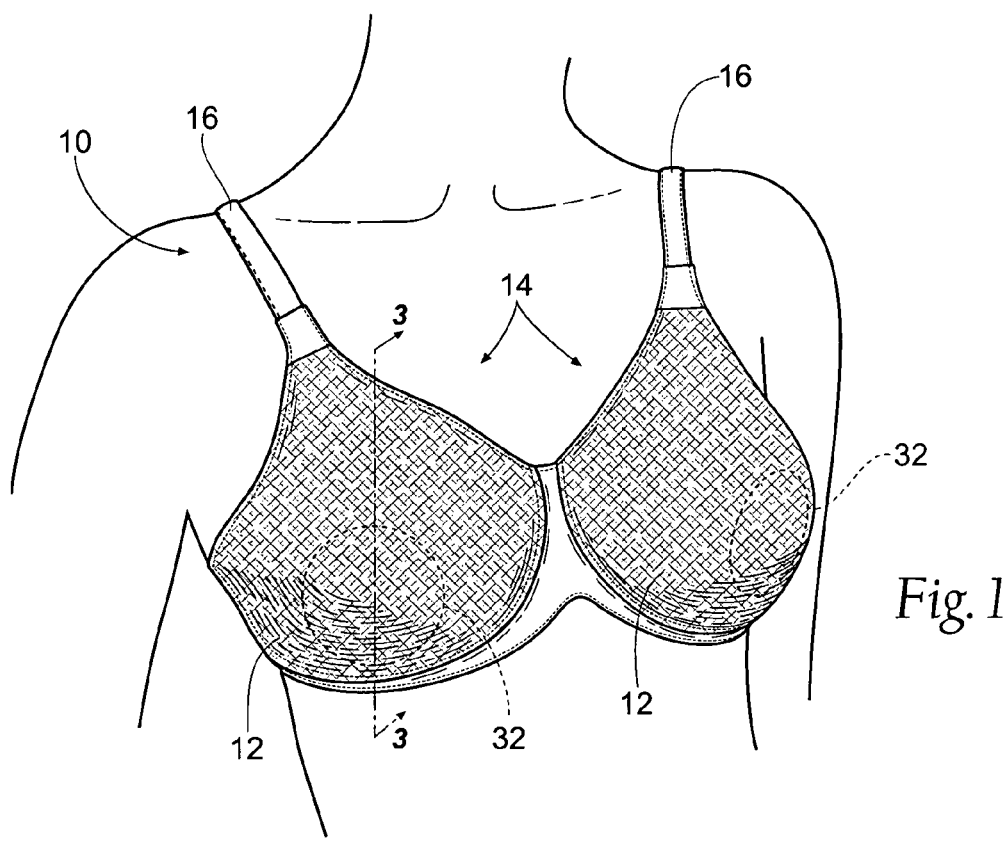
FIG. 1 is a front perspective view of nursing bra in accordance with the present invention.

Although the disclosure hereof is detailed and exact to enable those skilled in the art to practice the invention, the physical embodiments herein disclosed merely exemplify the invention which may be embodied in other specific structures. Like parts are referred to with like reference numerals. While the preferred embodiment has been described, the details may be changed without departing from the invention, which is defined by the claims.

FIG. 1 shows a nursing bra 10 having a pair of bra cups 12 that support a pair of breasts 14. A pair of straps 16 are attached to a respective cup 12 for securing said bra 10 to and over said breasts 14. It should be understood that the bra 10 could be in other shapes and forms as known in the art for nursing bras and still fall within the scope of the invention.

Figure 2:
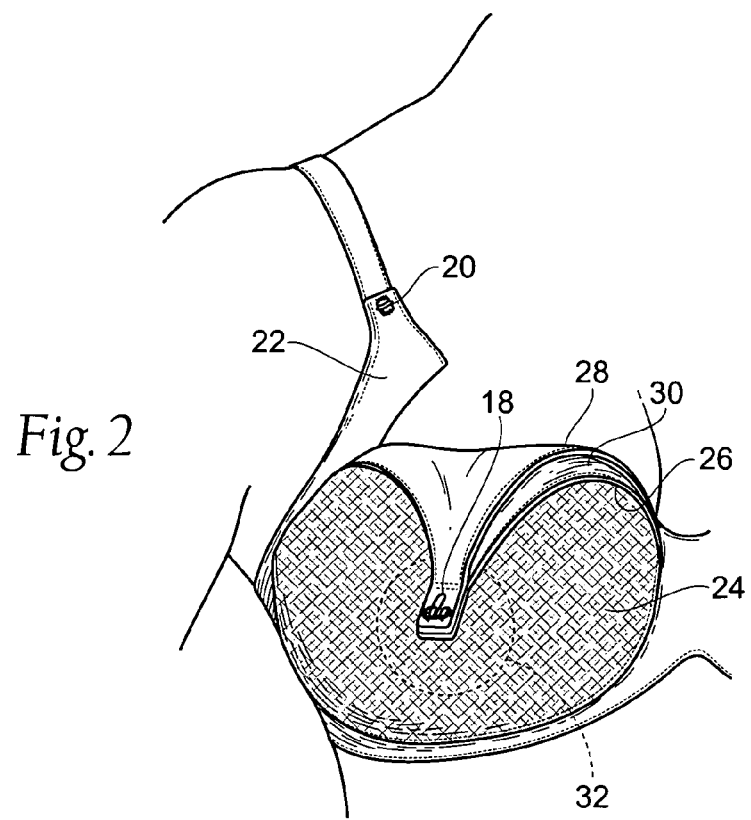
FIG. 2 shows a sectional front perspective view of the nursing bra of FIG. 1 showing an individual cup.

Referring to FIG. 2, one of the bra cups 12 is shown in a detached position. A latch, clasp, or other similar device 18 is removed from a locking member 20. The locking member 20 is located on an inner flap 22 of material and the latch is located on an outer flap of material 24. The arrangement of the latch 18 and the locking member 20 could be switched and still fall within the scope of the present invention. The inner flap 22 could be of any size or shape as desired for a specific bra shape. The outer flap 24 has an exterior flap of material 26 and an interior flap of material 28 that form a pocket 30. The pocket 30 holds a heating/cooling element 32.

Figure 3:
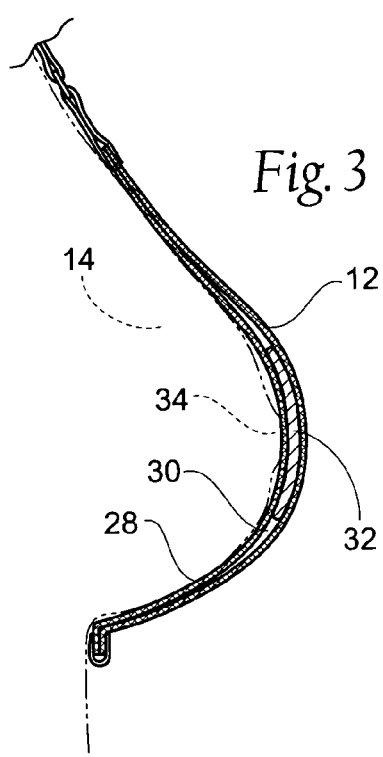
FIG. 3 is a side view of a nursing bra in accordance with the present invention.
Figure 4:
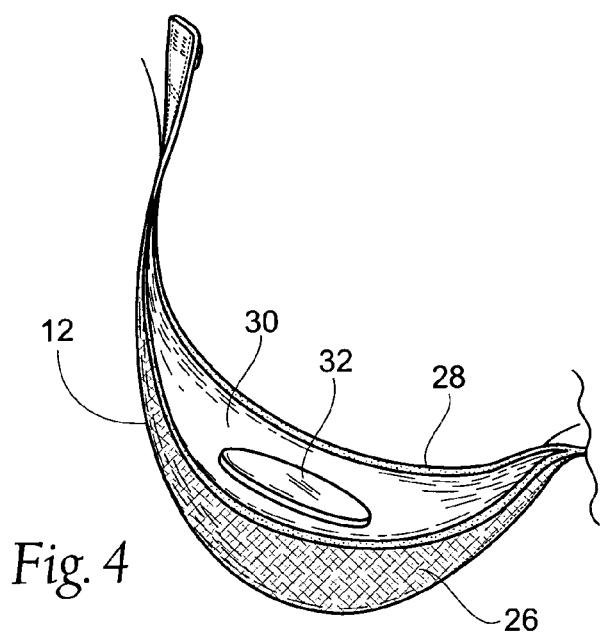
FIG. 4 is a perspective of an opened individual cup for a nursing bra in accordance with the present invention.

FIGS. 3 and 4 show further views of one of the bra cups 12. The heating/cooling element 32 sits within the pocket 30. As shown in FIG. 3, the heating/cooling element 32 preferably is centered within the pocket 30 around the nipple 34 of the breast 14. Preferably, the heating/cooling element 32 should cover most of the breast 14 to evenly reduce any pain or discomfort of the breast 14 while still protecting the breast 14 from any potential injury from the heating/cooling element 32. The interior piece of material 28 prevents the heating/cooling element 32 from coming into direct contact with either the breast 14 or the nipple 34. This is an advantage over the prior art by providing the necessary relief in a comfortable manner.

Figure 5:
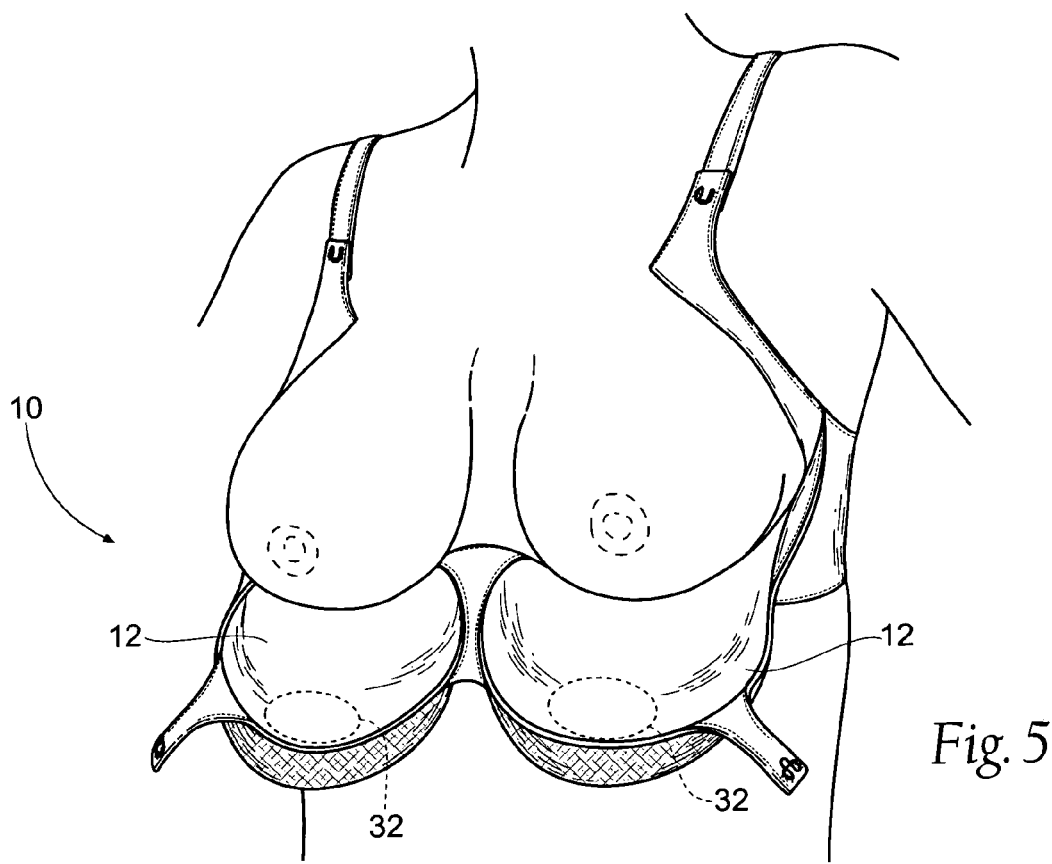
FIG. 5 is a front perspective view of the nursing bra of FIG. 1 in an open position.

FIG. 5 shows the bra 10 in a open position and is used to illustrate that either of the bra cups 12 may be attached. Further the heating/cooling element 32 or heating/cooling elements 32 are shown in phantom to further emphasize that the heating/cooling elements 32 are protected from the breasts 12 by the interior piece of material 28, which is beneficial for the comfort of the wearer.

The heating element 32 preferably a round shape and thin, with a gel substance, that does not freeze completely but will cool when necessary. Other devices, such as heating/cooling beads may be used. Preferably the element 32 is not visibly noticeable when worn.

The present invention has an additional piece of fabric that acts as a pocket for a heating/cooling device and a barrier that covers the entire breast. Due to leakage, these other products have a hole for the absorbent pad to have direct contact with the nipple. Therefore it would be unnecessary for these other bras to hold the heating cooling device because there would be direct skin to product contact, which would be uncomfortable for the wearer. Similarly, it would be unpractical for this invention to be used to hold an absorbent pad, because there is no hole and nothing to remove if leakage were to occur.

The present invention has several advantages over the prior art. The bra 10 accurately places heat to the entire desired area (breast or breasts), whereas prior vest arrangements may cover just a portion due to varied body shapes. Since the bra 10 is sized to fit the breasts 12, it will always cover the intended area. Also, the bra 10 allows you to feel the full effect of the warmth or cold because it is not placed over cloths or an undergarment and can be worn discreetly in public. Since the heating elements 32 may be located in separate pockets, a wearer can keep one side in place while nursing on the other, and will not get in the way when trying to nurse an infant, which would be more comfortable, since a nursing bra is constantly worn.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A nursing bra for supporting a pair of breasts, said bra comprising:
   a pair of bra cups, each of said bra cups comprising:
   an inner flap of material;
   an outer flap of material entirely coextensively covering said inner flap of material; said outer flap of material attached to said inner flap of material; said outer flap exposing one of said breasts when detached from said inner flap of material;
   means for securing said bra to and over said breasts;
   at least one pocket being in contact with at least one of said breasts, said pocket covering essentially the entire breast; and
   at least one heating/cooling element, said heating/cooling element being receivable within said pocket, said heating/cooling element being entirely separated from direct contact with said breast by said pocket.

2. The nursing bra according to claim 1 further comprising a pair of pockets, each of said pockets being affixed to one of said bra cups and being in contact with one of said pair of breasts, each of said pocket covering substantially one of the entire breasts.

3. The nursing bra according to claim 2 wherein each of said pockets is affixed to a respective outer flap of material.

4. The nursing bra according to claim 3 wherein said pockets are integrally formed with said outer flap of material.

5. The nursing bra according to claim 2 further comprising a pair of heating elements, each of said heating/cooling elements being receivable within one of said pockets, each of said heating/cooling element being entirely separated from direct contact with said breast by said pocket.

6. The nursing bra according to claim 1 wherein said heating/cooling element comprise a a thin, circular element.

7. The nursing bra according to claim 1 wherein said heating/cooling element is movable within said pocket.

8. A nursing bra for supporting a pair of breasts, said bra comprising:
   a pair of bra cups, each of said bra cups comprising:
   an inner flap of material;
   an outer flap of material entirely coextensively covering said inner flap of material; said outer flap of material attached to said inner flap of material; said outer flap exposing one of said breasts when detached from said inner flap of material;
   a pocket connected to said outer flap of material, said pocket being in direct contact with said breast, said pocket covering essentially the entire breast;
   means for securing said bra to and over said breasts; and
   at least one heating/cooling element, said heating/cooling element being receivable within one of said pockets, said heating/cooling element being entirely separated from direct contact with said breast by said pocket.

9. The nursing bra according to claim 8 further comprising a pair of heating/cooling elements, each of said heating/cooling element being receivable within one of said pockets, each of said heating/cooling element being entirely separated from direct contact with said breast by said pocket.

10. The nursing bra according to claim 8 wherein at least one of said pockets is integrally formed with one of said outer flaps of material.

11. The nursing bra according to claim 8 wherein said heating/cooling element comprises a thin circular element.

12. A nursing bra for supporting a pair of breasts, said bra comprising:
    a pair of bra cups, each of said bra cups comprising:
    an inner flap of material;
    an outer flap entirely coextensively covering said inner flap of material, said outer flap of material attached to said inner flap of material, said outer flap exposing one of said breasts when detached from said inner flap of material, said outer flap comprising an exterior piece of material and an interior piece of material;
    a pocket being formed by said exterior piece of material and said interior piece of material, said pocket being in direct contact with said breast, said pocket covering essentially the entire breast;
    means for securing said bra to and over said breasts; and
    at least one heating/cooling element, said heating/cooling element being located within one of said pockets, said heating/cooling element being entirely separated from direct contact with said breast by said pocket, said heating element evenly heating/cooling said breast.

13. The nursing bra according to claim 12 further comprising a pair of heating/cooling elements, each of said heating/cooling elements being located within one of said respective pockets, each of said heating/cooling element being entirely separated from direct contact with said breast by said pocket.

14. The nursing bra according to claim 13 wherein said heating/cooling elements are removable from said pockets.

15. The nursing bra according to claim 12 wherein said heating/cooling element is a thin, circular element.

16. The nursing bra according to claim 12 wherein said heating/cooling element is movable within said pocket.

17. The nursing bra according to claim 12 wherein said heating/cooling element is a gel substance, said gel substance forming a non-freezable material.

* * * * *